(12) United States Patent
McKeon et al.

(10) Patent No.: US 8,425,439 B1
(45) Date of Patent: Apr. 23, 2013

(54) LOCKING AND RELEASING HINGE

(76) Inventors: Brian P. McKeon, Essex, MA (US);
John D. Fiegener, Marblehead, MA (US)

( * ) Notice: Subject to any disclaimer, the term of this patent is extended or adjusted under 35 U.S.C. 154(b) by 207 days.

(21) Appl. No.: 12/622,037

(22) Filed: Nov. 19, 2009

Related U.S. Application Data

(60) Provisional application No. 61/116,205, filed on Nov. 19, 2008.

(51) Int. Cl.
*A61F 5/00* (2006.01)
(52) U.S. Cl.
USPC .................. 602/16; 16/324; 16/326; 16/334; 602/5
(58) Field of Classification Search ................ 602/5, 16, 602/23, 26; 16/324, 326, 334
See application file for complete search history.

(56) References Cited

U.S. PATENT DOCUMENTS

| | | | | |
|---|---|---|---|---|
| 5,074,290 A | * | 12/1991 | Harris et al. | 602/16 |
| 5,188,584 A | * | 2/1993 | Petrofsky et al. | 602/16 |
| 6,325,773 B1 | * | 12/2001 | Opel | 602/26 |

* cited by examiner

*Primary Examiner* — Patricia Bianco
*Assistant Examiner* — Camtu Nguyen
(74) *Attorney, Agent, or Firm* — Fish & Richardson P.C.

(57) ABSTRACT

A lockable hinge assembly configured for incorporation within a brace for stabilizing a joint includes a static support structure configured to remain in a fixed position, a dynamic support structure that is configured to be rotatable relative to the dynamic support structure, and a locking means for locking the dynamic support structure in a desired fixed position relative to the static support structure. The locking means is configured to enable the dynamic support structure to rotate relative to the static support structure and to automatically lock the dynamic support structure in a fixed position relative to the static support structure when the dynamic support structure rotates into the desired position.

19 Claims, 13 Drawing Sheets

LOCKING AND RELEASING HINGE

CROSS REFERENCE TO RELATED APPLICATION

This application claims priority to U.S. Provisional Patent Application Ser. No. 61/116,205, filed on Nov. 19, 2008 and entitled "Locking and Releasing Hinge," which is incorporated herein by reference in its entirety.

TECHNICAL FIELD

This disclosure relates to a locking and releasing hinge, and, more particularly, to a locking and releasing hinge for incorporation within a brace (e.g., a knee brace).

BACKGROUND

A patient may wear a brace (e.g., a knee brace or an ankle brace) to provide extra support to a joint while recovering from an injury or surgery to the joint. Similarly, an athlete may wear a brace to provide extra support to a joint while exercising or participating in athletic competition.

SUMMARY

A hinge for incorporation into a brace (e.g., a knee brace) that enables a wearer of the brace to lock the brace at a desired angle and also to unlock the brace to allow free rotation is disclosed. Implementations may be capable of quick locking/unlocking while being fully capable of unlocking for extended periods of time until the wearer determines that the brace should be locked at a desired angle.

In one general aspect, a lockable hinge assembly configured for incorporation within a brace for stabilizing a joint of a human being includes a locking mechanism having a substantially cylindrical body and a plurality of anchoring segments that extend radially from the body of the locking mechanism as well as a base having a top surface on which a plurality of guidewalls are formed that extend upward from the top surface of the base and that define a substantially cylindrical-shaped interior opening configured to receive the body of the locking mechanism. The plurality of guidewalls define gaps therebetween, and the gaps between the guidewalls are configured to receive the anchoring segments of the locking mechanism. The gaps between the guidewalls also open into stopping slots that are formed within the guidewalls. The stopping slots are configured to receive the anchoring segments of the locking mechanism such that, when the anchoring segments of the locking mechanism are received within the gaps, the stopping slots are accessible to the anchoring segments of the locking mechanism by rotating the locking mechanism. The hinge assembly also includes a static plate within which an interior opening is formed that is configured to receive the guidewalls of the base and the cylindrical body of the locking mechanism. The static plate also is configured to be fixed in a constant position relative to the base. In addition, the hinge assembly includes a dynamic plate within which an interior opening is formed that is configured to receive the cylindrical body of the locking mechanism. A plurality of locking teeth extend from the dynamic plate into the interior opening formed within the dynamic plate. The plurality of locking teeth define a plurality of locking teeth gaps therebetween. The locking teeth gaps are configured to receive the anchoring segments of the locking mechanism and define one or more lockable positions for locking the dynamic plate in a fixed position relative to the static plate and the base. The hinge assembly further includes a spring that is positioned between the top surface of the base and the locking mechanism and that is configured to exert a force on the locking mechanism in a direction that is opposite from the top surface of the first base. When the locking mechanism is rotated to a position such that the anchoring segments of the locking mechanism are received within the stopping slots formed within the guidewalls of the base, the force exerted by the spring on the locking mechanism is prevented from enabling the anchoring segments of the locking mechanism to engage the locking teeth gaps formed in the dynamic plate, thereby allowing the dynamic plate to be rotated. In contrast, when the locking mechanism is rotated to a position such that the anchoring segments of the locking mechanism are not received within the stopping slots formed within the guidewalls of the base, the force exerted by the spring on the locking mechanism enables the anchoring segments of the locking mechanism to engage the locking teeth gaps formed in the dynamic plate and lock the dynamic plate in a fixed position relative to the static plate and the base.

Implementations may include one or more of the following features. For example, at least one of the dynamic plate and the static plate may be formed from stainless steel. Additionally or alternatively, at least one of the dynamic plate and the static plate may be formed from aluminum. Furthermore, the interior opening formed in the static plate and the interior opening formed within the dynamic plate may be of substantially the same area.

In some implementations, one or more knobs may extend upward from a top surface of the locking mechanism, and these knobs may be configured to facilitate rotation of the locking mechanism to rotate the anchoring segments into and out of the stopping slots formed within the guidewalls of the anchor base. Furthermore, the hinge assembly also may include a top panel positioned above the dynamic plate, and one or more openings may be formed in the top panel. The one or more openings formed in the top panel each may be configured to receive an individual one of the knobs extending from the top surface of the locking mechanism in a manner that enables a received knob to be rotated within the opening in the top panel.

In some implementations, the hinge assembly may include a spacer ring positioned between the dynamic plate and the top panel, and the spacer ring may be configured to reduce friction between the dynamic plate and the top panel when the dynamic plate is rotated. In such implementations, the spacer ring may be formed at least partially from polytetrafluoroethylene.

A top panel guide structure also may be formed on and extend upward from the top surface of the base, and one or more receiving slots may be formed within the top panel guide structure. In addition, one or more protrusions may be formed on and extend downward from a bottom surface of the top panel, and each of the one or more protrusions may be configured to mate with a corresponding receiving slot formed within the top panel guide structure.

Furthermore, in some implementations, a countersunk screw hole may be formed within the top panel guide structure of the base and configured to receive a screw. In addition, a screw hole may be formed on a bottom surface of the top panel and configured to secure a screw. In such implementations, the lockable hinge assembly may be secured together by a screw that is threaded through the countersunk screw hole formed in the top panel of the guide structure and that extends into the screw hole formed on the bottom surface of the top panel.

In some implementations, the locking teeth gaps may define a position for locking the dynamic plate in a fixed position of flexion and/or the locking teeth gaps may define a position for locking the dynamic plate in a fixed position of extension. For example, the locking teeth gaps may define a position for locking the dynamic plate at an angle of substantially 0° relative to the static plate.

The dynamic plate may be positioned above the static plate, and the hinge assembly may include a spacer ring that is positioned between the dynamic plate and the static plate. The spacer ring may be configured to reduce friction between the static plate and the dynamic plate when the dynamic plate is rotated. In such implementations, the spacer ring may be formed at least partially from polytetrafluoroethylene.

In some implementations, a plurality of static plate locking protrusions may be formed on and extend outward from the top surface of the base. Furthermore, a plurality of static plate locking teeth may extend from the static plate into the interior opening formed within the static plate such that the plurality of static plate locking teeth define a plurality of static plate locking gaps therebetween. In addition, each of the static plate locking gaps may engage a corresponding one of the static plate locking protrusions, thereby locking the static plate in a fixed position relative to the base.

The static plate may be integrally formed within a lateral strut configured to be incorporated within a knee brace such that the lateral strut extends in a lateral direction from a wearer's knee towards the wearer's foot. Additionally or alternatively, the dynamic plate may be integrally formed within a lateral strut configured to be incorporated within a knee brace such that the lateral strut extends in a lateral direction from a wearer's knee towards the wearer's hip.

In another general aspect, a knee brace includes an upper support member for engaging a portion of a wearer's leg above the wearer's knee and a lower support member for engaging a portion of a wearer's leg below the wearer's knee. In addition, the knee brace includes a first hinge assembly and a second hinge assembly. The first hinge assembly includes a first locking mechanism having a substantially cylindrical body and a first plurality of anchoring segments that extend radially from the body of the first locking mechanism as well as a first base having a top surface on which a first plurality of guidewalls are formed that extend upward from the top surface of the first base and define a substantially cylindrical-shaped interior opening configured to receive the body of the first locking mechanism. The first plurality of guidewalls also define gaps therebetween, and the gaps between the first guidewalls are configured to receive the first anchoring segments of the first locking mechanism. In addition, the gaps between the first guidewalls open into first stopping slots that are formed within the first guidewalls. The first stopping slots are formed within the first guidewalls and are configured to receive the first anchoring segments of the first locking mechanism such that, when the first anchoring segments of the first locking mechanism are received within the first gaps, the first stopping slots are accessible to the first anchoring segments of the first locking mechanism by rotating the first locking mechanism. The first hinge assembly also includes a first static strut operably connected to the lower support member at one position along the first static strut's length and having a first static plate at another position along the length of the first static strut. An interior opening is formed within the first static plate and configured to receive the first guidewalls of the first base and the cylindrical body of the first locking mechanism. The first static strut also is configured to be fixed in a constant position relative to the first base. The first hinge assembly further includes a first dynamic strut operably connected to the upper support member at one position along the first static strut's length and having a first dynamic plate at another position along the length of the first dynamic strut. An interior opening is formed within the first static plate and is configured to receive the cylindrical body of the first locking mechanism. A first plurality of locking teeth extend from the first dynamic plate into the interior opening formed within the first dynamic plate such that the first plurality of locking teeth define a first plurality of locking teeth gaps therebetween. The first locking teeth gaps are configured to receive the first anchoring segments of the first locking mechanism and define one or more lockable positions for locking the first dynamic strut in a fixed position relative to the first static strut and the first base. In addition, the first hinge assembly also includes a first spring positioned between the top surface of the first base and the first locking mechanism. The first spring is configured to exert a force on the first locking mechanism in a direction that is opposite from the top surface of the first base. When the first locking mechanism is rotated to a position such that the first anchoring segments of the first locking mechanism are received within the first stopping slots formed within the first guidewalls of the first base, the force exerted by the first spring on the first locking mechanism is prevented from enabling the first anchoring segments of the first locking mechanism to engage the first locking teeth gaps formed in the first dynamic plate, thereby allowing the first dynamic strut to be rotated. In contrast, when the first locking mechanism is rotated to a position such that the first anchoring segments of the first locking mechanism are not received within the first stopping slots formed within the first guidewalls of the first base, the force exerted by the first spring on the first locking mechanism enables the first anchoring segments of the first locking mechanism to engage the first locking teeth gaps formed in the first dynamic plate, thereby locking the first dynamic strut in a fixed position relative to the first static strut and the first base. The knee brace further includes a second hinge assembly including a second locking mechanism having a substantially cylindrical body and a second plurality of anchoring segments that extend radially from the body of the second locking mechanism, and a second base having a top surface on which a second plurality of guidewalls are formed that extend upward from the top surface of the second base and that define a substantially cylindrical-shaped interior opening configured to receive the body of the second locking mechanism. The second plurality of guidewalls define gaps therebetween, and the gaps between the second guidewalls are configured to receive the second anchoring segments of the second locking mechanism. In addition, the gaps between the second guidewalls open into second stopping slots that are formed within the second guidewalls. The second stopping slots formed within the second guidewalls are configured to receive the second anchoring segments of the second locking mechanism such that, when the second anchoring segments of the second locking mechanism are received within the second gaps, the second stopping slots are accessible to the second anchoring segments of the second locking mechanism by rotating the second locking mechanism. The second hinge assembly also includes a second static strut that is operably connected to the lower support member at one position along the second static strut's length and that has a second static plate at another position along the length of the second static strut. An interior opening is formed within the second static plate and is configured to receive the second guidewalls of the second base and the cylindrical body of the second locking mechanism. In addition, the second static strut is configured to be fixed in a constant position relative to the second base.

The second hinge assembly also includes a second dynamic strut that is operably connected to the upper support member at one position along the second dynamic strut's length and that has a second dynamic plate at another position along the length of the second dynamic strut. An interior opening is formed within the second static plate and is configured to receive the cylindrical body of the second locking mechanism. A second plurality of locking teeth extend from the second dynamic plate into the interior opening formed within the second dynamic plate such that the second plurality of locking teeth define a second plurality of locking teeth gaps therebetween. The second locking teeth gaps are configured to receive the second anchoring segments of the second locking mechanism and define one or more lockable positions for locking the second dynamic strut in a fixed position relative to the second static strut and the second base. Furthermore, the second hinge assembly includes a second spring that is positioned between the top surface of the second base and the second locking mechanism and that is configured to exert a force on the second locking mechanism in a direction that is opposite from the top surface of the second base. When the second locking mechanism is rotated to a position such that the second anchoring segments of the second locking mechanism are received within the second stopping slots formed within the second guidewalls of the second base, the force exerted by the second spring on the second locking mechanism is prevented from enabling the second anchoring segments of the second locking mechanism to engage the second locking teeth gaps formed in the second dynamic plate, thereby allowing the second dynamic strut to be rotated. In contrast, when the second locking mechanism is rotated to a position such that the second anchoring segments of the second locking mechanism are not received within the second stopping slots formed within the second guidewalls of the second base, the force exerted by the second spring on the second locking mechanism enables the second anchoring segments of the second locking mechanism to engage the second locking teeth gaps formed in the second dynamic plate and lock the second dynamic strut in a fixed position relative to the second static strut and the second base.

In yet another general aspect, a lockable hinge assembly configured for incorporation within a knee brace for stabilizing a knee of a human being includes a static support structure configured to remain in a fixed position, a dynamic support structure that is configured to be rotatable relative to the dynamic support structure, and a locking means for locking the dynamic support structure in a desired fixed position relative to the static support structure. The locking means is configured to enable the dynamic support structure to rotate relative to the static support structure and to automatically lock the dynamic support structure in a fixed position relative to the static support structure when the dynamic support structure rotates into the desired position.

The details of one or more implementations are set forth in the accompanying drawings and the description below. Other features will be apparent from the description and drawings, and from the claims.

DETAILED DESCRIPTION

A hinge is disclosed. In some implementations, the hinge may be incorporated into a knee brace to be worn by a patient rehabilitating from knee surgery and/or by an athlete during participation in exercise or athletic competition.

Figure 1:
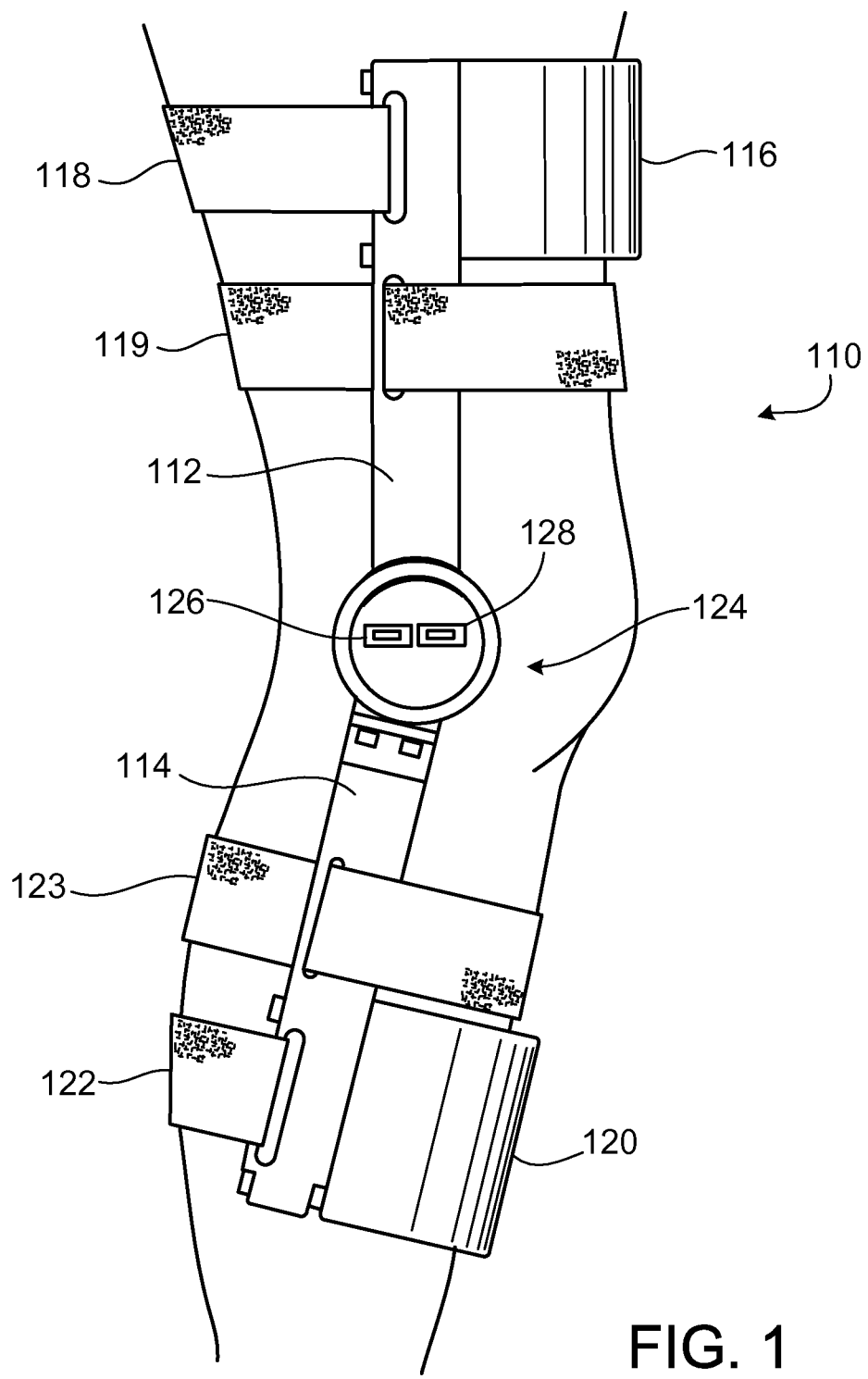
FIG. 1 is a side view of an example of a knee brace including a hinge.

For example, referring to FIG. 1, there is shown a side view of an example of a knee brace 110 including a hinge 124. Although only one side of the knee brace 10 is shown in the figure, it will be appreciated that the other side of the knee brace 110 may include the same parts and have the same configuration of the side that is shown. The knee brace 110 includes upper struts 112, lower struts 114, an upper anterior femur/thigh support member 116, an upper posterior femur/thigh support member 118, a lower anterior leg support member 120, a lower posterior leg support member 122, and hinge assembly 124. The upper struts 112 and lower struts 114 may be made from a strong, durable material, such as, for example, stainless steel, aluminum, or plastic.

The upper strut 112, which will be described in greater detail below in connection with FIG. 7, generally comprises a rigid elongated member having one or more fastening structures at one end. An opening is formed in one end of the upper strut 112 to receive a portion of the upper posterior femur/thigh support member 118. In some implementations, the upper strut 112 may include additional openings, for example in order to receive a second upper posterior femur/thigh support member 119. A pair of locking bolts may be configured to operably attach the upper strut 112 to the upper anterior femur/thigh support member 16.

Similarly, the lower strut 114, which will be described in greater detail below in connection with FIG. 9, generally comprises a rigid elongated member having one or more fastening structures at one end. An opening is formed in one end of the lower strut 114 to receive a portion of the lower posterior leg support member 122. In some implementations, the lower strut 114 may include additional openings, for example in order to receive a second lower posterior leg support member 123. A pair of locking bolts may be configured to operably attach the lower strut 114 to the lower anterior leg support member 120.

Upper anterior femur/thigh support structure 116 and lower anterior leg support structure 120 may be configured in the same shape as shown, although their respective dimensions may differ to accommodate the differing structures of the thigh and calf area. In addition, the support structures 116 and 120 comprise outer bodies formed from a rigid, light weight material such as aluminum or plastics and inner fabric or cushion linings (such as, for example, felt) to increase comfort and wearability of the knee brace 110.

The upper posterior femur/thigh support member 118 and the lower posterior leg support member 122 (as well as the optional members 119 and 123) may be straps formed from a fabric material that can wrap around the wearer's leg and pass through the respective openings of the upper 112 and lower 114 struts. The support members 118 and 122 also may include a hook and loop fastener, such that the strap members 118 and 122 can wrap around the wearer's leg and pass through the respective openings of the upper 112 and lower 114 struts and be secured upon themselves. Additional strut openings also may be formed in the upper and lower struts 112 and 114 to accept additional straps 119 and 123 as shown in FIG. 1.

In some implementations, the upper anterior femur/thigh support member 116 and the upper posterior femur/thigh support member 118 may comprise a single member formed of a rigid material, such as aluminum or plastic, that is secured to the upper strut 112. Similarly, the lower anterior leg support member 120 and lower posterior leg support member 122 may comprise a single member formed of a rigid material, such as aluminum or plastic, that is secured to the lower strut 114. These singular members may include buckle type fasteners to lock the respective support members to the thigh and calf area of a wearer's leg.

The knee brace 110 is generally configured to form a relatively rigid structure about the knee of the wearer. In this regard, the knee brace 110 supports the stress placed upon the wearer's knee and serves to lock the wearer's knee at a desired angle during use. The lateral struts 112 and 114 lock into place through a spring loaded locking system on the inside of the hinge assembly 124. A compression spring enables the hinge 124 to lock automatically with a push on one or two push knobs 126 and 128.

In order to unlock the hinge 124 and enable the wearer to bend his/her knee, the two knobs 126 and 128 may be pushed down and rotated slightly in the counter-clockwise direction. This rotation may keep the hinge 124 unlocked until the push knobs 126 and 128 are rotated in the clockwise direction. In some implementations, if the push knobs 126 and 128 have been rotated clockwise out of the unlocked position, even if the hinge 124 is not at a lockable angle, the hinge 124 may automatically lock to the next closest lockable location. An audible click may confirm the locking action. One or more portions of the hinge assembly 124 may be made of a strong, light-weight, and corrosive resistant metal, such as, for example, stainless steel or aluminum.

The brace 110 including hinge 124 may enable a surgeon or other medical professional to lock a patient's knee in extension shortly after knee surgery with relative ease. For example, the hinge 124 may be configured to have a lockable location in a position of extension (e.g., at a position of 0-10°). In such an implementation, the knee brace 110 including hinge 124 enables the surgeon or medical professional to place the patient's knee into the brace 110 when the hinge 124 is unlocked and to gently push the patient's knee into extension. When the patient's knee reaches the lockable location corresponding to a position of extension, the hinge 124 automatically locks, thereby locking the patient's knee into extension.

Likewise, the brace 110 including hinge 124 may enable a wearer's knee to be locked into a desired angle of flexion, which may be desirable in some forms of athletic competition. For example, the brace 110 including hinge 124 may be worn by a golfer to keep the golfer's right knee (left knee for a left handed golfer) at a constant angle during a swing—facilitating proper take away, correct weight transfer, and desirable balance throughout the swing—while unlocking after the swing to provide the golfer the ability to walk to and set up for the next shot. In such implementations, the hinge 124 may accommodate various levels of knee flexion depending upon the golfer, the shot presented, and the conditions present (e.g. height, arm, and leg length of the golfer, course conditions, ball lie, angle of land slope, and playing hazards). The hinge may operate in both a locked position mode (restricting the golfer from changing the knee flexion angle during the shot) and an unlocked, adjustable rotation mode (allowing the golfer to freely walk from hole to hole without interference and difficulty).

Stabilizing a golfer's right knee (left knee for a left handed golfer) during the full motion of the golfer's golf swing may help the golfer keep the golfer's knee flexion angle constant throughout the swing. Proper knee flexion may be important during all phases of the golf swing. From the first phase—the take away phase—to the third phase—the follow through phase—maintenance of a critical knee flexion angle may help to keep the golfer's swing in the correct line of action.

The take away phase of the golf swing involves bringing the club to the overhead position. If the critical knee flexion angle changes during the swing, the desired outcome may not be reached. For example, there may be unwanted vertical motion, potentially preventing the golfer from achieving correct club location. Any changes in this knee angle also may result in improper loading of the right side (left side for a left-handed golfer); an aspect of golf that is vital to hitting the ball to the target location.

The second phase, the impact phase, of the golf swing requires a constant critical knee flexion angle in order to prevent undesired weight transfer. With a constant knee flexion angle, the golfer can properly transfer his/her weight from his/her right side to his/her left side (from his/her left side to his/her right side for a left-handed golfer) for impact. If the critical angle is not maintained for this part of the swing, there can be improper weight transfer.

In addition to undesired vertical motion and improper weight transfer, inadequate balance also may affect a golfer's swing. In the third phase, the follow through phase, improper balance may result if the golfer does not maintain the proper knee flexion angle. With improper balance, the golfer may fail to follow through properly, potentially resulting in errant shots. Proper golf swing mechanics generally result from proper stance and body position, including the right knee (left knee for a left handed golfer).

Implementations of a brace 110 including hinge 124 may enhance a golfer's ability to properly hit a golf ball and have the correct knee angle for all three phases of the golf swing by providing an accommodating hinge which aids the golfer in controlling and stabilizing the swing mechanics. Once a golfer's next shot is known, and the golfer is preparing for the swing, the hinge may be locked in a desired position to keep the golfer's knee at a desired flexion angle. Upon completion of the shot, the brace may be unlocked, providing the golfer with unlimited (or at least increased) ambulation and allowing him/her to walk to the next ball location.

It also will be appreciated that the hinge 124 may be incorporated into a knee brace 110 to be worn by a football player, a baseball player, a weightlifter and/or various other different types of athletes.

Figure 2:
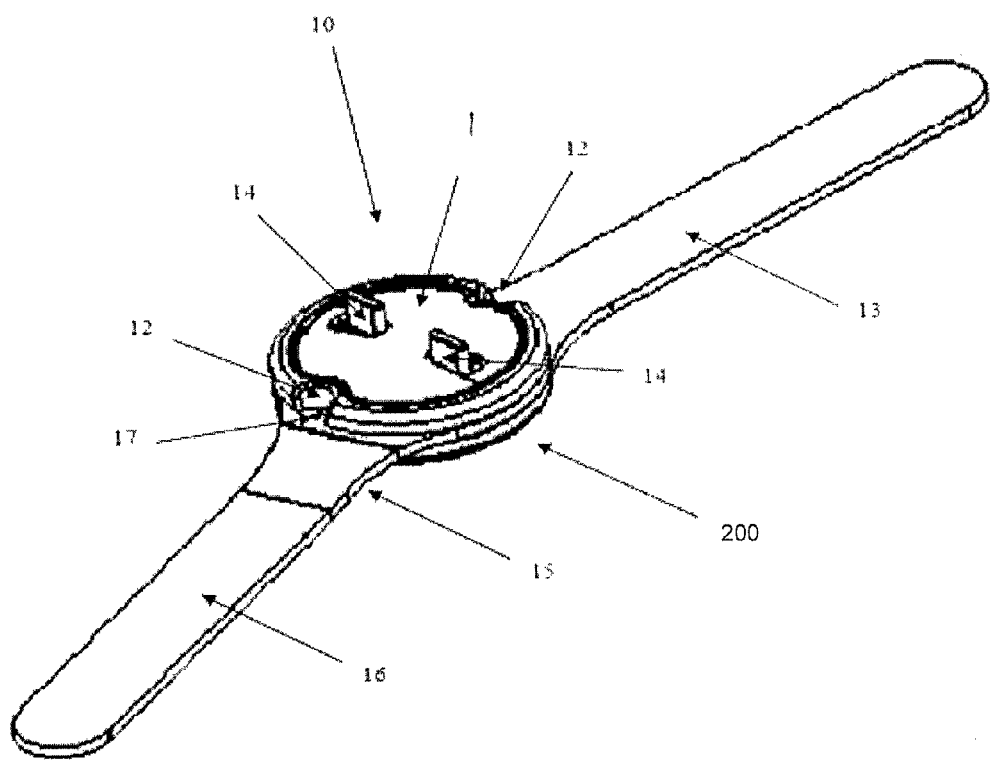
FIG. 2 is a perspective view of an example of a hinge assembly.

Implementations of a hinge for incorporation within a knee brace are now described in greater detail with reference to FIGS. 2-11B. Referring to FIG. 2, there is seen a hinge 10 for incorporation within a knee brace (not shown). The adjustable hinge 10, while capable of locking the knee in place, is further capable of unlocking to allow full, unrestricted ambulation. The hinge 10 may be incorporated within a knee brace, such as, for example, the knee brace disclosed in applicant's U.S. Pat. No. 6,361,448 (which is incorporated herein by reference in its entirety), in order to stabilize a wearer's knee through two extended arms: the dynamic support 16 and the static support 13.

The hinge 10 includes a center assembly 200 that allows for adjustment of the hinge 10 through the rotation of push knobs 14. Seen in FIG. 4, the push knobs 14 have trigger slots 18 in which they slide to either lock or unlock the hinge. The center assembly 200 also has two semi-circular gaps (flexion gaps) 12 which provide a user with a mechanism for reading the setting 17, marked here by A. These markings 17 allow the user to adjust the hinge 10 to different lockable locations.

Figure 3:
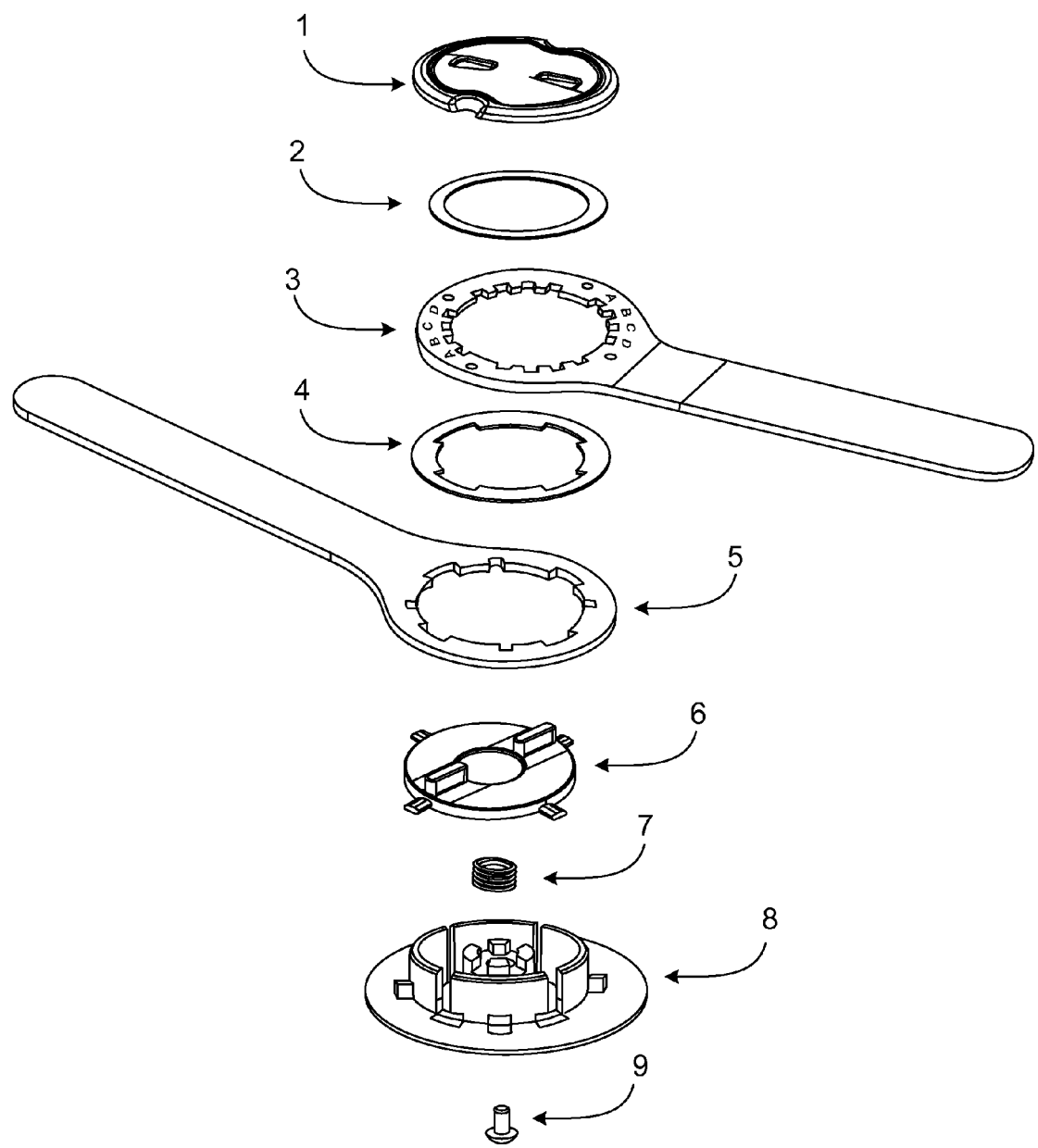
FIG. 3 is an exploded view of the hinge assembly of FIG. 2.
Figure 4:
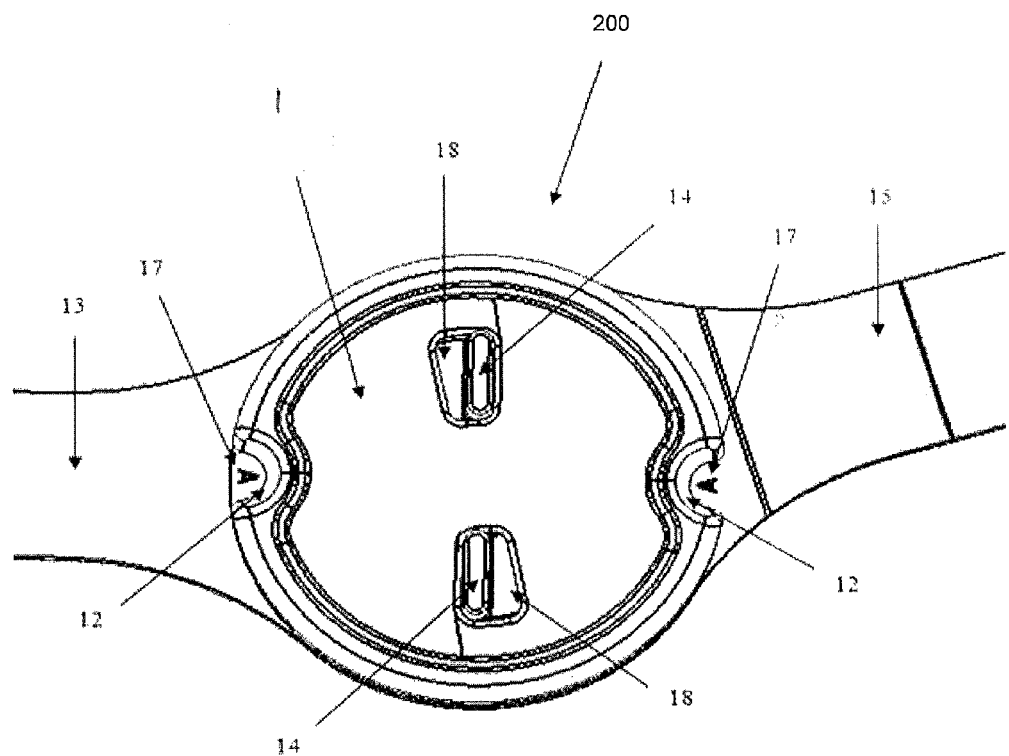
FIG. 4 is a front view of the center of the hinge assembly of FIG. 2.

These settings 17 are marked on the dynamic plate 3 seen in FIG. 3, which is an exploded view of the hinge 10. The front panel 1 is configured to mate with an upper spacer 2 which lies on top of the dynamic plate 3. A lower spacer 4 is configured to fit underneath the dynamic plate 3 and on top of the static plate 5. All of these previous pieces define center holes. The push knob trigger 6 is configured to fit through these center holes, eventually engaging the two top trigger slots 18 in the front panel 1. A compression spring 7 is configured to fit below the push knob trigger 6 and on a center extrusion of the anchor base 8. A push screw 9, which fits into slots defined in the anchor base 8 and the front panel 1, locks the assembly together.

Figure 5A:
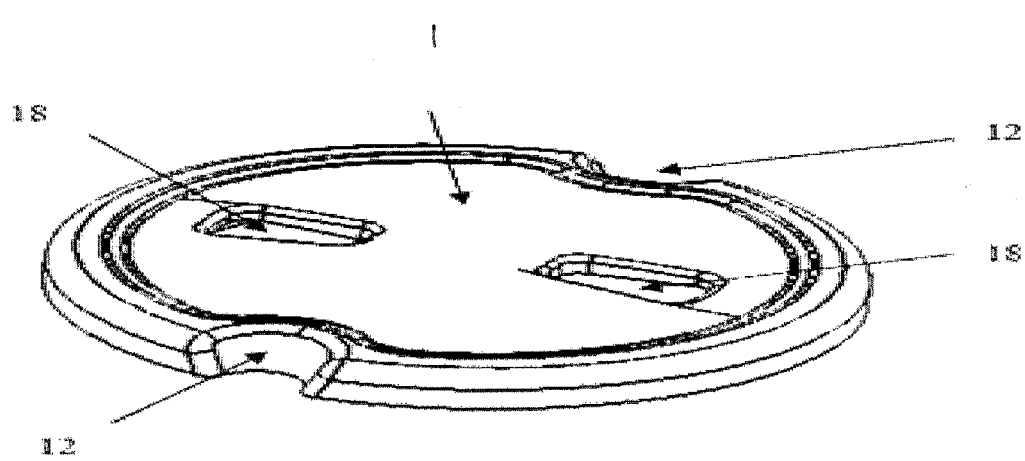
FIGS. 5A and 5B are views of an example of a front panel of a knee hinge assembly.
Figure 5B:
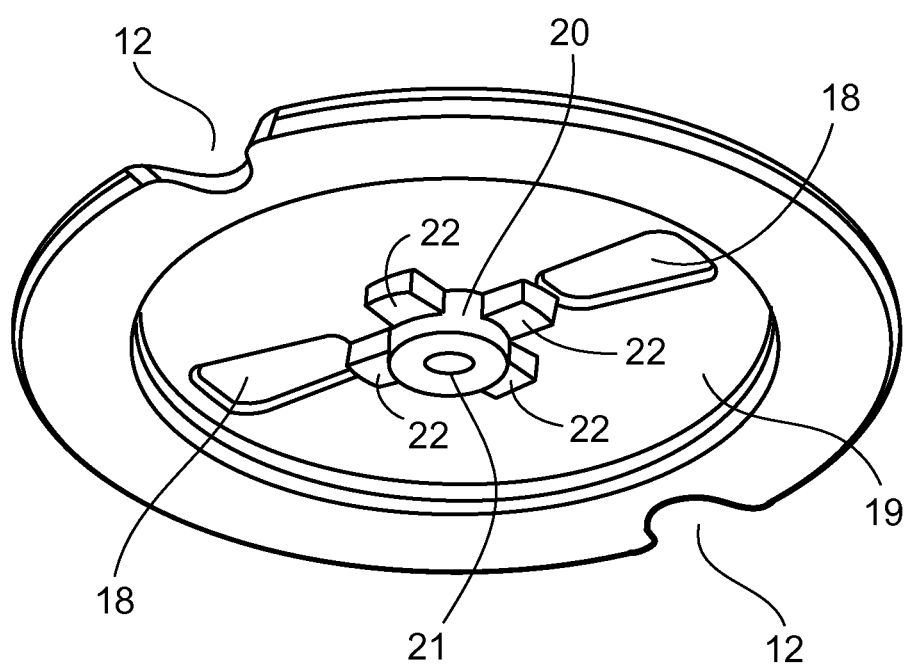

The front panel 1, seen in FIG. 5A may have a smooth surface, enabling the user to easily adjust the settings. The two flexion gaps 12 also allow the user to see the setting in which the hinge 10 is positioned. The underside 19 of the front panel 1, seen in FIG. 5B, has a cylindrical extension 20 and defines a hole (front panel screw hole) 21 for the push screw 9 to fit in and lock the assembly together. Four rectangular extensions (front panel guides) 22 extend radially off of this cylindrical extension 20, maintaining the front panel in line with the push knob trigger 6 and preventing the push knobs 14 from rotating in the slots 18 until pressure is applied to the push knobs 14.

Figure 6:
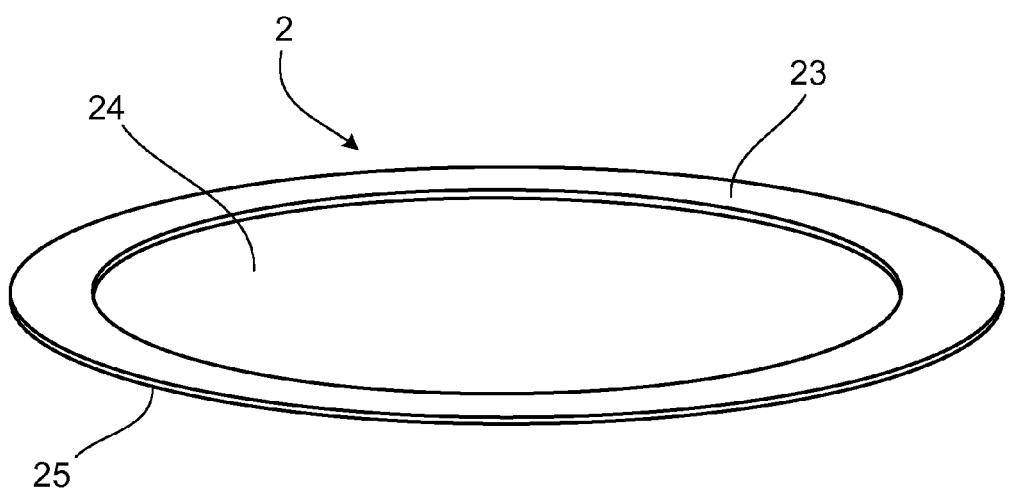
FIG. 6 is a view of an example of an upper spacer of a knee hinge assembly.

The upper spacer 2 is illustrated in FIG. 6. The upper spacer 2 has a substantially circular shape that defines a hole in the center 24 to allow other components to fit through. The upper spacer 2 may be made from or coated with a durable, friction reducing material such as, for example, polytetrafluoroethylene (e.g., TEFLON®), and serves to separate the front panel 1 from dynamic plate 3, while limiting friction and wear on the front panel 1 and dynamic plate 3 when the hinge 10 rotates.

Figure 7:
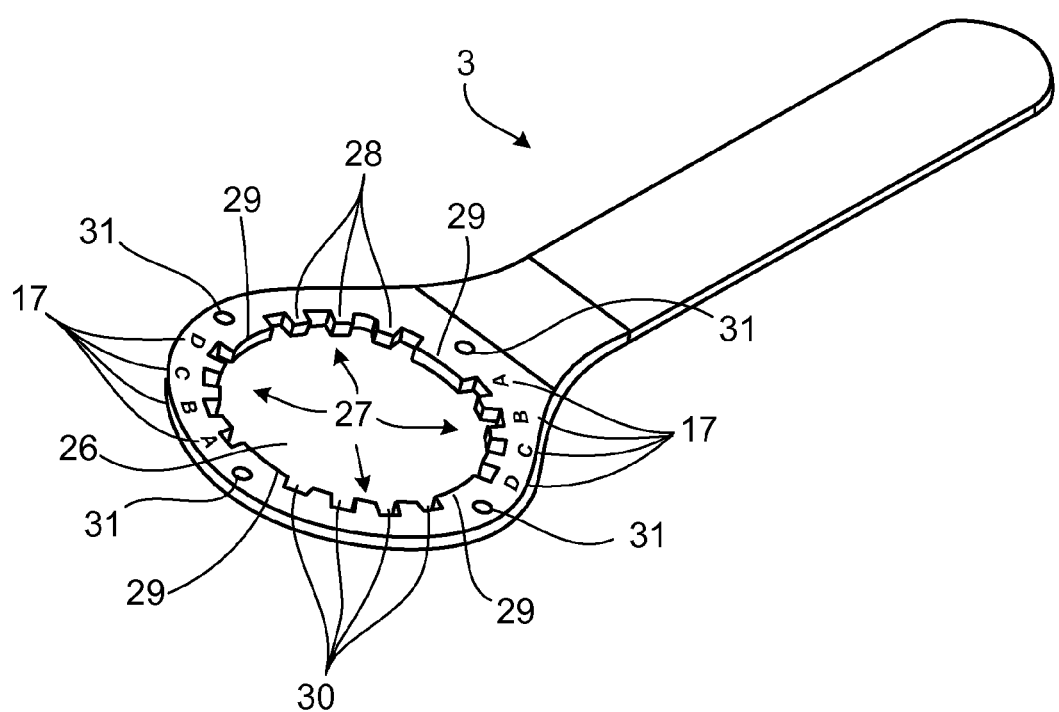
FIG. 7 is a view of an example of a dynamic plate for a knee hinge assembly.

FIG. 7 shows the dynamic plate 3. The dynamic plate 3 also defines a circular hole in the middle (dynamic plate ring) 26 through which other components fit when the hinge 10 is assembled. Along this inner ring 26, four dynamic teeth sections 27 are formed, each section having three teeth (dynamic teeth) 28. Separating these dynamic teeth sections 27 are four larger teeth (dynamic separators) 29. In some implementations, these dynamic separators 29 may be equally spaced around the inner ring 26. The formation of this dynamic plate 3 permits the hinge 10 to lock at each different tooth by receiving an anchoring segment 40 formed on the push knob trigger 6 at the tooth, making for numerous different angled, locked positions. Along the surface of this plate are several markings 17, ranging from A to D, indicating the different lockable settings for the hinge 10. These lockable settings correspond to the tooth gaps 30 defined by the dynamic teeth, where the hinge 10 is capable of locking in place. Placed at the dynamic separators 29, a "0" marking 31 is seen, indicating a place where the hinge may not lock.

Figure 8:
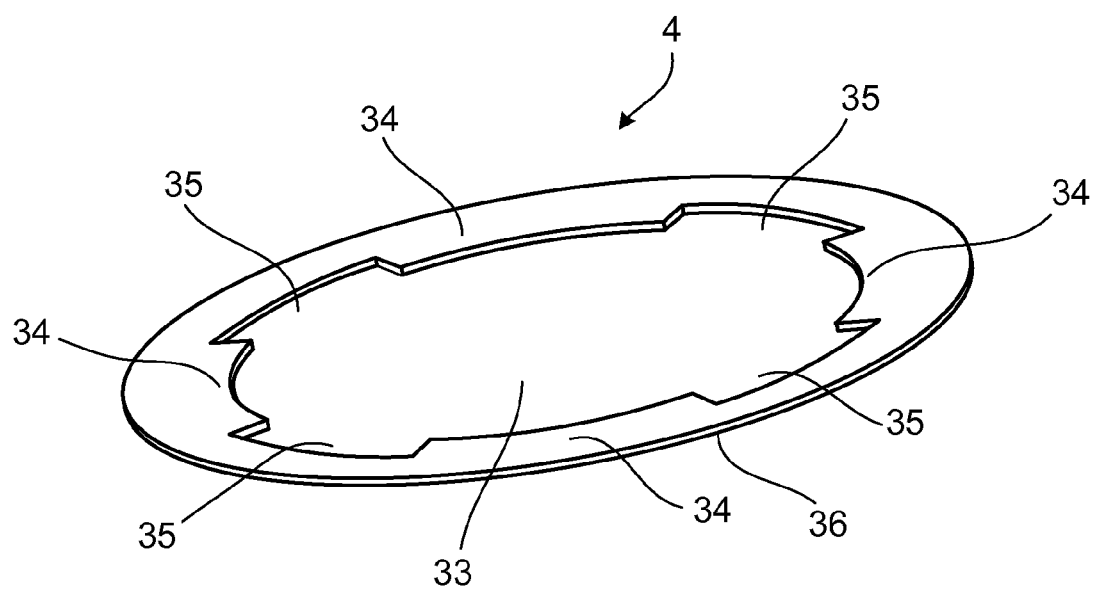
FIG. 8 is a view of an example of a lower spacer of a knee hinge assembly.

Another spacer (lower spacer) 4, seen in FIG. 8, is located beneath the dynamic plate 3. The lower spacer 4 may fit between the dynamic plate 3 and static plate 5. Similar to the upper spacer 2, the lower spacer 2 may serve to separate the dynamic plate 3 and static plate 5 and provide a smooth, friction reducing section on which the plates rotate. For this reason, the lower spacer 4 may be constructed from or be coated with a material with lubrication qualities, such as, for example, polytetrafluoroethylene (e.g., TEFLON®). The lower spacer 4, although similar to the upper spacer 2 may have a different construction than the upper spacer 2. For example, four spacer slots 35 are cut into the inner ring 33 of the lower spacer 4 and configured to allow the anchoring segments 40 of the push knob trigger 6 to fit and slide without obstruction. In some implementations, the four spacer slots 35 may be equally spaced around the inner ring 33 of the lower spacer.

Figure 9:
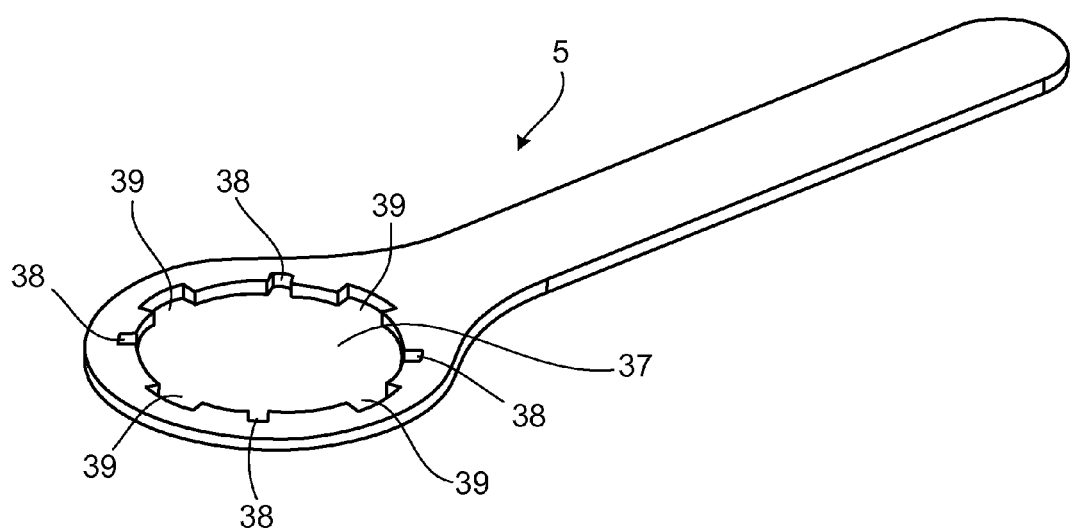
FIG. 9 is a view of an example of a static plate of a knee hinge assembly.

The static plate 5, seen in FIG. 9, is the counterpart to the dynamic plate 3. The static plate 5 may be of a similar design to the dynamic plate 3, but there are some variations. For example, the static plate 5 has fewer gaps along its inner ring 37. As illustrated in FIG. 9, there are four radial cuts (the static gaps) 38 and four smaller, rectangular cuts (static plate locks) 39. In some implementations, the static gaps may be equally spaced around the inner ring 37 of the static plate 5 and/or the static plate locks 39 may be equally spaced around the inner ring 37 of the static plate 5. Each of the static plate locks 39 corresponds to an extrusion 49 on the anchor base 8. These matching extrusions 49 on the anchor base 8 are received within the static plate locks 39, thus causing the static plate 5 to be locked in a constant position relative to the anchor base 8 while the dynamic plate 3 may rotate to achieve different positions. The static gaps 38 are configured to align with the dynamic teeth sections 27 of the dynamic plate 3 to enable the anchoring segments 40 of the push knob trigger 6 to slide within and pass through the inner ring 37 of the dynamic plate 5 and engage the dynamic teeth 28 of the dynamic plate 3 to lock the hinge 10.

Figure 10:
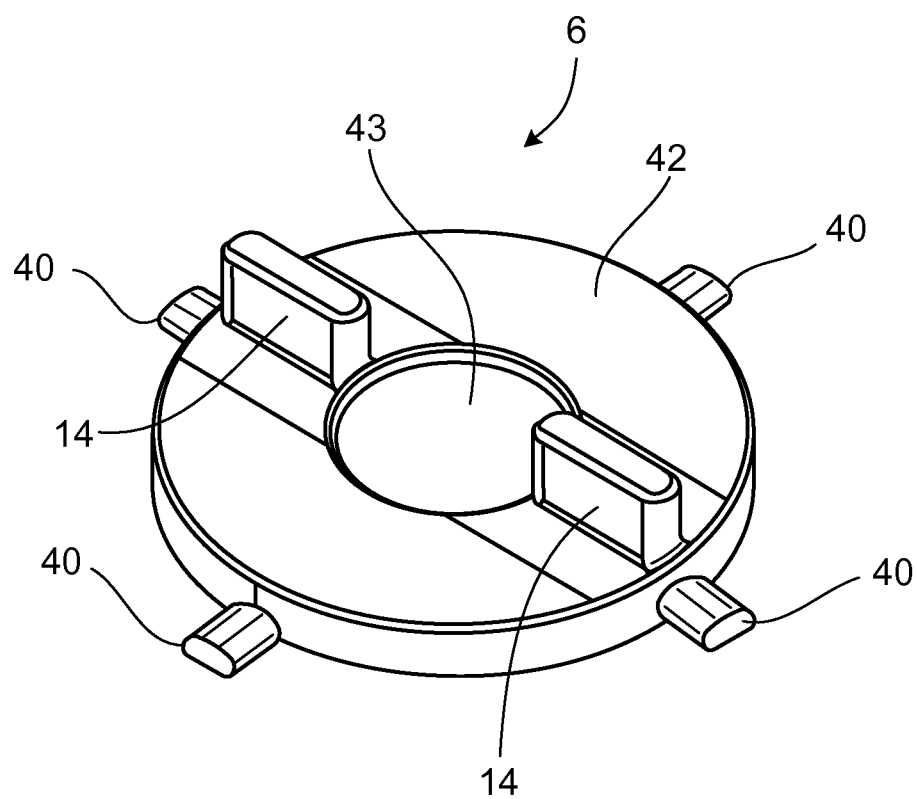
FIG. 10 is a perspective view of an example of a push knob trigger for a knee hinge assembly.

FIG. 10 shows the push knob trigger 6. The push knob trigger 6 has a cylindrical shape defining a trigger ring 43 in its center. Along the push knob trigger's top face 42 and off-set by 180°, push knobs 14 extrude out. These push knobs 14 are configured to be able to be pushed and rotated in order to lock and unlock the hinge 10. Toward the bottom of the cylindrical push knob trigger 6, four anchoring segments 40 extend radially outward and are configured to slide into corresponding slots 44 in the anchor base 8.

Between the push knob trigger 6 and the anchor base 8 rests a compression spring 7, which may enable the hinge 10 to lock in a position, even if the user does not lock the hinge 10 with the hinge positioned at an actual lockable setting. This aspect of the hinge 10 may enable the user to lock the brace even without looking at the setting by automatically locking the hinge 10 at the next closest lockable position.

Figure 11A:
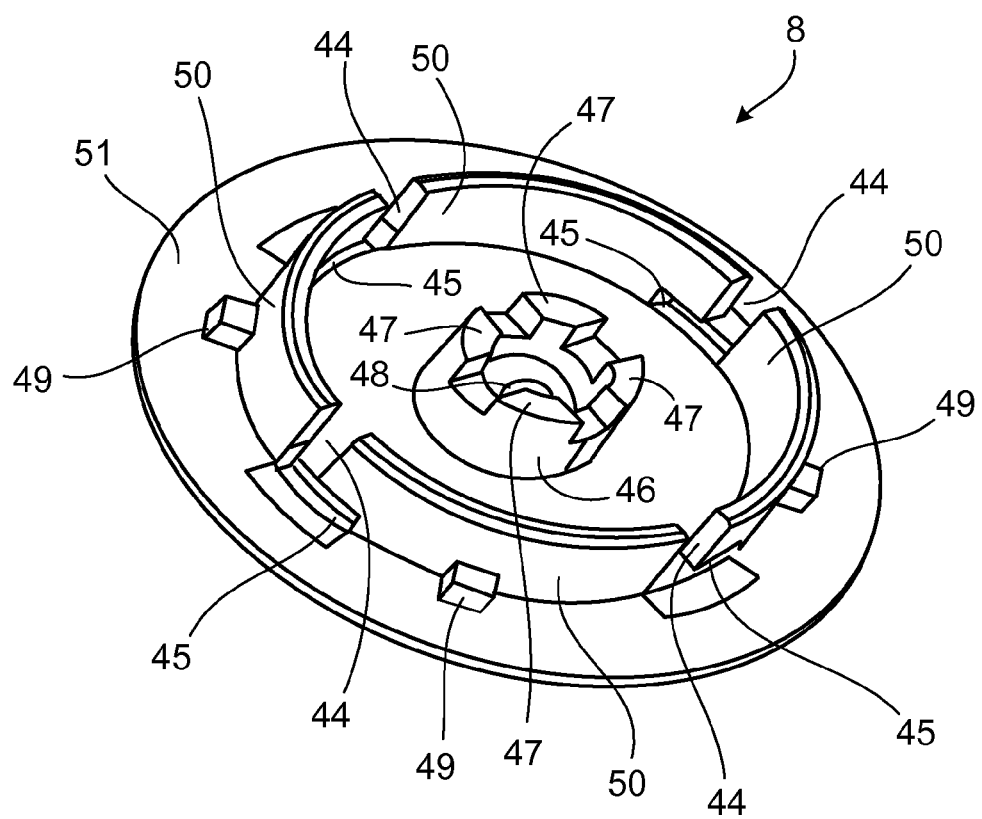
FIGS. 11A and 11B are views of top and bottom surfaces of an example of an anchor base for a knee hinge assembly.

The push knob trigger 6 has four anchoring segments 40 that slide into four anchoring slots 44 along the anchor base 8. FIG. 11A shows the top surface 51 of the anchor base 8. In the center of the anchor base 8, the guide cylinder 46 extrudes outward, with an anchor screw hole 48 defined in the center and four quasi-trapezoidal guides 47 coming off the top. The guide cylinder 46 is configured to mate with the front panel guides 22 of the front panel 1. Further out from the center of the anchor base 8, four side walls 50 extend from the top surface 51 of the anchor base 8. These walls 50 are separated from each other by the four previously mentioned anchoring slots 44. At the base of each slot 44 is a horizontally cut stop slot 45 extending to the right. Each of these horizontal stop slots 45 keeps the hinge unlocked and allows for full ambulation and adjustment until the push knobs 14 are rotated to the locking position. This rotation causes the anchoring segments 40 on the push knob trigger 6 to slide out of the horizontal stop slots 45 and the compression spring 7 forces the anchoring extrusions upward along the anchoring slots 44 until the anchoring slots are received in corresponding teeth gaps defined in the inner ring 26 of the dynamic plate 3, thus causing the hinge 10 to lock at the desired setting.

Figure 11B:
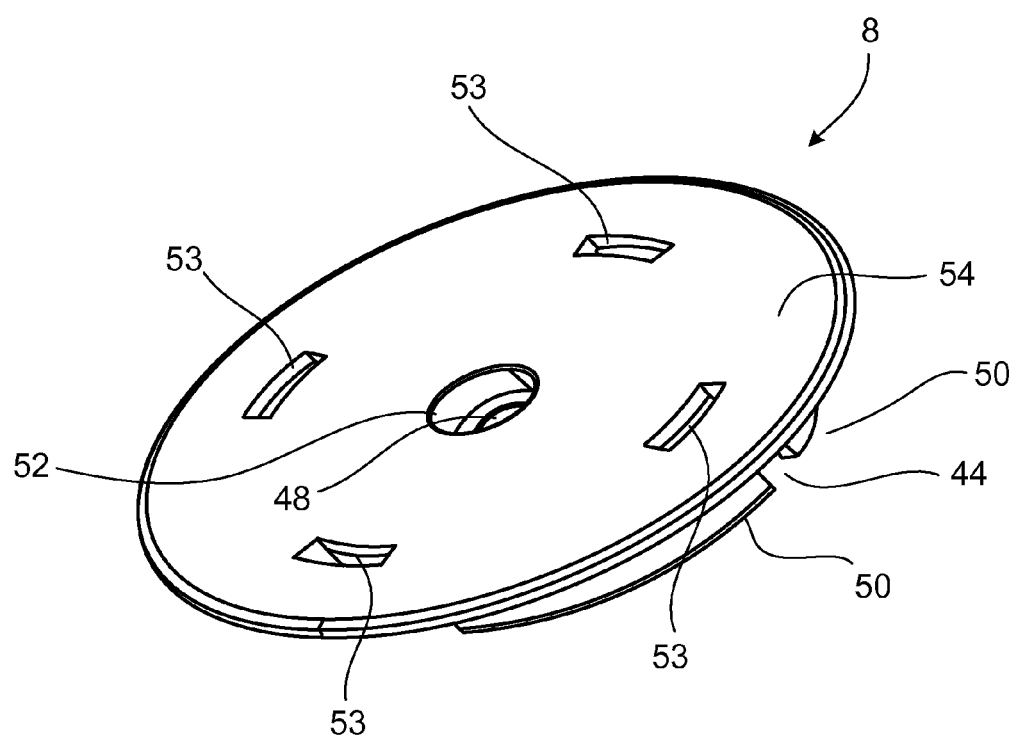

The underneath of the anchor base 54 is seen in FIG. 11B. A countersunk hole 52 is formed in the center of the anchor base 54 and configured to receive the push screw 9. This screw countersink 52 may prevent any part of the screw 9 from extending outward toward the inner side of the brace and the medial side of the leg. The front panel screw hole 21 formed in the front panel 1 is configured to receive and secure the screw 9, thus providing a mechanism by which the components of the hinge 10 may be fastened together. Also seen on the anchor base underside 54 are four vents 53. These vents 53 may allow for a slight view of the inside of the hinge 10 enabling the user to look for any obstructions. For example, the vents 53 may permit the user to see the anchoring segments 40 of the push knob trigger 6 which lock the hinge 10 in position. To fasten the entire hinge assembly together, the push screw 9 is inserted in the countersunk hole 52 and screwed into position.

A number of implementations have been described. Nevertheless, it will be understood that various modifications may be made. For example, although the dynamic support of the hinge has been described chiefly as being intended to be incorporated within the upper half of a knee brace and the static support of the hinge has been described chiefly as being intended to be incorporated within the lower half of a knee brace, the dynamic support may be incorporated within the lower half of a knee brace and the static support may be incorporated within the upper half of a knee brace. Furthermore, in some implementations, a single hinge may be incorporated within a knee brace, whereas in other implementations, two hinges may be incorporated within a knee brace. Accordingly, other implementations are within the scope of the following claims.

What is claimed is:

1. A lockable hinge assembly configured for incorporation within a brace for stabilizing a joint of a human being, the hinge comprising:
    a locking mechanism having a substantially cylindrical body and a plurality of anchoring segments that extend radially from the body of the locking mechanism;
    a base having a top surface on which a plurality of guidewalls are formed that extend upward from the top surface of the base and define a substantially cylindrical-shaped interior opening configured to receive the body of the locking mechanism, the plurality of guidewalls defining gaps therebetween, the gaps between the guidewalls being configured to receive the anchoring segments of the locking mechanism, and the gaps also opening into stopping slots that are formed within the guidewalls, the stopping slots formed within the guidewalls being configured to receive the anchoring segments of the locking mechanism such that, when the anchoring segments of the locking mechanism are received within the gaps, the stopping slots are accessible to the anchoring segments of the locking mechanism by rotating the locking mechanism;
    a static plate within which an interior opening is formed that is configured to receive the guidewalls of the base and the cylindrical body of the locking mechanism, the static plate being configured to be fixed in a constant position relative to the base;
    a dynamic plate within which an interior opening is formed that is configured to receive the cylindrical body of the locking mechanism, a plurality of locking teeth extending from the dynamic plate into the interior opening formed within the dynamic plate, the plurality of locking teeth defining a plurality of locking teeth gaps therebetween, the locking teeth gaps being configured to receive the anchoring segments of the locking mechanism and defining one or more lockable positions for locking the dynamic plate in a fixed position relative to the static plate and the base; and
    a spring positioned between the top surface of the base and the locking mechanism and configured to exert a force on the locking mechanism in a direction that is opposite from the top surface of the first base, wherein:
    when the locking mechanism is rotated to a position such that the anchoring segments of the locking mechanism are received within the stopping slots formed within the guidewalls of the base, the force exerted by the spring on the locking mechanism is prevented from enabling the anchoring segments of the locking mechanism to engage the locking teeth gaps formed in the dynamic plate, allowing the dynamic plate to be rotated, and
    when the locking mechanism is rotated to a position such that the anchoring segments of the locking mechanism are not received within the stopping slots formed within the guidewalls of the base, the force exerted by the spring on the locking mechanism enables the anchoring segments of the locking mechanism to engage the locking teeth gaps formed in the dynamic plate and lock the dynamic plate in a fixed position relative to the static plate and the base.

2. The lockable hinge assembly of claim 1 wherein one or more knobs extend upward from a top surface of the locking mechanism, the one or more knobs being configured to facilitate rotation of the locking mechanism to rotate the anchoring segments into and out of the stopping slots formed within the guidewalls of the anchor base.

3. The lockable hinge assembly of claim 2 further comprising a top panel positioned above the dynamic plate, one or more openings being formed in the top panel, the one or more openings formed in the top panel each being configured to receive an individual one of the knobs extending from the top surface of the locking mechanism and enabling a received knob to be rotated within the opening in the top panel.

4. The lockable hinge assembly of claim 3 further comprising a spacer ring positioned between the dynamic plate and the top panel, the spacer ring being configured to reduce friction between the dynamic plate and the top panel when the dynamic plate is rotated.

5. The lockable hinge assembly of claim 4 wherein the spacer ring is formed at least partially from polytetrafluoroethylene.

6. The lockable hinge assembly of claim 3 wherein:
    a top panel guide structure is formed on and extends upward from the top surface of the base, one or more receiving slots being formed within the top panel guide structure;
    one or more protrusions are formed on and extend downward from a bottom surface of the top panel, each of the one or more protrusions being configured to mate with a corresponding receiving slot within the one or more receiving slots formed within the top panel guide structure.

7. The lockable hinge assembly of claim 6 wherein:
   a countersunk screw hole is formed within the top panel guide structure of the base and configured to receive a screw; and
   a screw hole is formed on a bottom surface of the top panel and configured to secure a screw, the lockable hinge assembly further comprising a screw threaded through the countersunk screw hole formed in the top panel guide structure and extending into the screw hole formed on the bottom surface of the top panel, where the screw is secured.

8. The lockable hinge assembly of claim 1 wherein the locking teeth gaps define a position for locking the dynamic plate in a fixed position of flexion.

9. The lockable hinge assembly of claim 1 wherein the locking teeth gaps define a position for locking the dynamic plate in a fixed position of extension.

10. The lockable hinge assembly of claim 9 wherein the locking teeth gaps that define a position for locking the dynamic plate in a fixed position of extension define a position for locking the dynamic plate at an angle of substantially 0° relative to the static plate.

11. The lockable hinge assembly of claim 1 wherein the dynamic plate is positioned above the static plate, the lockable hinge assembly further comprising a spacer ring positioned between the dynamic plate and the static plate, the spacer ring being configured to reduce friction between the static plate and the dynamic plate when the dynamic plate is rotated.

12. The lockable hinge assembly of claim 1 wherein a spacer ring is formed at least partially from polytetrafluoroethylene.

13. The lockable hinge assembly of claim 1 wherein at least one of the dynamic plate and the static plate is formed from stainless steel.

14. The lockable hinge assembly of claim 1 wherein at least one of the dynamic plate and the static plate is formed from aluminum.

15. The lockable hinge assembly of claim 1 wherein the interior opening formed in the static plate and the interior opening formed within the dynamic plate are of substantially the same size.

16. The lockable hinge assembly of claim 1 wherein:
   a plurality of static plate locking protrusions are formed on and extend outward from the top surface of the base; and
   a plurality of static plate locking teeth extend from the static plate into the interior opening formed within the static plate, the plurality of static plate locking teeth defining a plurality of static plate locking gaps therebetween, each of the static plate locking gaps engaging a corresponding one of the static plate locking protrusions and locking the static plate in a fixed position relative to the base.

17. The lockable hinge assembly of claim 1 wherein the static plate is integrally formed within a lateral strut configured to be incorporated within a knee brace such that the lateral strut extends in a lateral direction from a wearer's knee towards the wearer's foot.

18. The lockable hinge assembly of claim 1 wherein the dynamic plate is integrally formed within a lateral strut configured to be incorporated within a knee brace such that the lateral strut extends in a lateral direction from a wearer's knee towards the wearer's hip.

19. A knee brace comprising:
   an upper support member for engaging a portion of a wearer's leg above the wearer's knee;
   a lower support member for engaging a portion of a wearer's leg below the wearer's knee;
   a first hinge assembly including:
      a first locking mechanism having a substantially cylindrical body and a first plurality of anchoring segments that extend radially from the body of the first locking mechanism;
      a first base having a top surface on which a first plurality of guidewalls are formed that extend upward from the top surface of the first base and define a substantially cylindrical-shaped interior opening configured to receive the body of the first locking mechanism, the first plurality of guidewalls defining gaps therebetween, the gaps between the first guidewalls being configured to receive the first anchoring segments of the first locking mechanism and the gaps also opening into first stopping slots that are formed within the first guidewalls, the first stopping slots formed within the first guidewalls being configured to receive the first anchoring segments of the first locking mechanism such that, when the first anchoring segments of the first locking mechanism are received within the first gaps, the first stopping slots are accessible to the first anchoring segments of the first locking mechanism by rotating the first locking mechanism;
      a first static strut operably connected to the lower support member at one position along the first static strut's length and having a first static plate at another position along the length of the first static strut, an interior opening being formed within the first static plate and configured to receive the first guidewalls of the first base and the cylindrical body of the first locking mechanism, the first static strut being configured to be fixed in a constant position relative to the first base;
      a first dynamic strut operably connected to the upper support member at one position along the first static strut's length and having a first dynamic plate at another position along the length of the first dynamic strut, an interior opening being formed within the first static plate and configured to receive the cylindrical body of the first locking mechanism, a first plurality of locking teeth extending from the first dynamic plate into the interior opening formed within the first dynamic plate, the first plurality of locking teeth defining a first plurality of locking teeth gaps therebetween, the first locking teeth gaps being configured to receive the first anchoring segments of the first locking mechanism and defining one or more lockable positions for locking the first dynamic strut in a fixed position relative to the first static strut and the first base; and
      a first spring positioned between the top surface of the first base and the first locking mechanism and configured to exert a force on the first locking mechanism in a direction that is opposite from the top surface of the first base, wherein:
         when the first locking mechanism is rotated to a position such that the first anchoring segments of the first locking mechanism are received within the first stopping slots formed within the first guidewalls of the first base, the force exerted by the first spring on the first locking mechanism is prevented from enabling the first anchoring segments of the first locking mechanism to engage the first locking teeth gaps formed in the first dynamic plate, allowing the first dynamic strut to be rotated, and when the first locking mechanism is rotated to a position such that the first anchoring segments of the first locking mechanism are not received within the first stopping slots formed within the first guidewalls of the first base, the force exerted by the first spring on the first locking mechanism enables the first anchoring segments of the first locking mechanism to engage the first locking teeth gaps formed in the first dynamic plate and lock the first dynamic strut in a fixed position relative to the first static strut and the first base; and a second hinge assembly including:
 a second locking mechanism having a substantially cylindrical body and a second plurality of anchoring segments that extend radially from the body of the second locking mechanism;
 a second base having a top surface on which a second plurality of guidewalls are formed that extend upward from the top surface of the second base and define a substantially cylindrical-shaped interior opening configured to receive the body of the second locking mechanism, the second plurality of guidewalls defining gaps therebetween, the gaps between the second guidewalls being configured to receive the second anchoring segments of the second locking mechanism and opening into second stopping slots that are formed within the second guidewalls, the second stopping slots formed within the second guidewalls being configured to receive the second anchoring segments of the second locking mechanism such that, when the second anchoring segments of the second locking mechanism are received within the second gaps, the second stopping slots are accessible to the second anchoring segments of the second locking mechanism by rotating the second locking mechanism;
 a second static strut operably connected to the lower support member at one position along the second static strut's length and having a second static plate at another position along the length of the second static strut, an interior opening being formed within the second static plate and configured to receive the second guidewalls of the second base and the cylindrical body of the second locking mechanism, the second static strut being configured to be fixed in a constant position relative to the second base;
 a second dynamic strut operably connected to the upper support member at one position along the second dynamic strut's length and having a second dynamic plate at another position along the length of the second dynamic strut, an interior opening being formed within the second static plate and configured to receive the cylindrical body of the second locking mechanism, a second plurality of locking teeth extending from the second dynamic plate into the interior opening formed within the second dynamic plate, the second plurality of locking teeth defining a second plurality of locking teeth gaps therebetween, the second locking teeth gaps being configured to receive the second anchoring segments of the second locking mechanism and defining one or more lockable positions for locking the second dynamic strut in a fixed position relative to the second static strut and the second base; and
 a second spring positioned between the top surface of the second base and the second locking mechanism and configured to exert a force on the second locking mechanism in a direction that is opposite from the top surface of the second base, wherein:
  when the second locking mechanism is rotated to a position such that the second anchoring segments of the second locking mechanism are received within the second stopping slots formed within the second guidewalls of the second base, the force exerted by the second spring on the second locking mechanism is prevented from enabling the second anchoring segments of the second locking mechanism to engage the second locking teeth gaps formed in the second dynamic plate, allowing the second dynamic strut to be rotated, and
  when the second locking mechanism is rotated to a position such that the second anchoring segments of the second locking mechanism are not received within the second stopping slots formed within the second guidewalls of the second base, the force exerted by the second spring on the second locking mechanism enables the second anchoring segments of the second locking mechanism to engage the second locking teeth gaps formed in the second dynamic plate and lock the second dynamic strut in a fixed position relative to the second static strut and the second base.

* * * * *